(12) United States Patent
Egger

(10) Patent No.: US 8,334,522 B2
(45) Date of Patent: Dec. 18, 2012

(54) METHOD FOR THE QUANTITATIVE DETERMINATION OF THE CONCENTRATION OF FLUOROPHORES OF A SUBSTANCE IN A SAMPLE AND APPARATUS FOR CARRYING OUT THE SAME

(75) Inventor: Rafael Egger, Munich (DE)

(73) Assignee: LRE Medical GmbH, Munich (DE)

(*) Notice: Subject to any disclaimer, the term of this patent is extended or adjusted under 35 U.S.C. 154(b) by 490 days.

(21) Appl. No.: 12/616,811

(22) Filed: Nov. 12, 2009

(65) Prior Publication Data

US 2010/0117003 A1 May 13, 2010

(30) Foreign Application Priority Data

Nov. 13, 2008 (DE) .......................... 10 2008 057 115

(51) Int. Cl.
| | |
|---|---|
| F21V 9/16 | (2006.01) |
| G01J 1/58 | (2006.01) |
| G01T 1/10 | (2006.01) |
| G21H 3/02 | (2006.01) |
| G21K 5/00 | (2006.01) |
| H01J 65/06 | (2006.01) |
| H01J 65/08 | (2006.01) |

(52) U.S. Cl. ...................... 250/459.1; 356/417; 356/318; 250/252.1

(58) Field of Classification Search .............. 250/459.1, 250/458.1, 252.1
See application file for complete search history.

(56) References Cited

U.S. PATENT DOCUMENTS

| | | | | |
|---|---|---|---|---|
| 4,750,837 A | * | 6/1988 | Gifford et al. ................. | 356/417 |
| 5,097,135 A | | 3/1992 | Makino et al. | |
| 7,154,603 B2 | * | 12/2006 | Banks ........................... | 356/417 |
| 7,199,360 B1 | * | 4/2007 | Montagu ..................... | 250/252.1 |
| 2007/0215801 A1 | * | 9/2007 | Walsh et al. ................ | 250/252.1 |
| 2008/0014655 A1 | | 1/2008 | Horn | |
| 2008/0038835 A1 | | 2/2008 | Westphal et al. | |
| 2009/0261239 A1 | * | 10/2009 | Clancy et al. .............. | 250/252.1 |

FOREIGN PATENT DOCUMENTS

| | | |
|---|---|---|
| DE | 32 12 219 A1 | 11/1982 |
| DE | 40 26 564 C2 | 5/1993 |
| DE | 10 2004 047 593 A1 | 4/2006 |
| DE | 602 10 878 T2 | 11/2006 |
| DE | 10 2005 032 249 A1 | 1/2007 |
| DE | 695 35 254 T2 | 4/2007 |
| DE | 10 2007 008 850 A1 | 11/2007 |
| DE | 10 2004 051 830 B4 | 12/2007 |
| EP | 0 237 363 A2 | 9/1987 |
| EP | 1 775 565 A1 | 4/2007 |

* cited by examiner

*Primary Examiner* — David Porta
*Assistant Examiner* — Edwin Gunberg
(74) *Attorney, Agent, or Firm* — McCormick, Paulding & Huber LLP

(57) ABSTRACT

The invention concerns methods and apparatuses for quantitatively determining the concentration of fluorophores of a substance in a sample. A constant portion of the reference light of a reference light wave length ($\lambda_r$) emitted by a reference light source is coupled in by an optical element in the direction of a receiving element. A first value corresponding to the portion of the reference light coupled in which is incident on the receiving element is detected. The sample is irradiated with the excitation light of an excitation wave length ($\lambda_{ex}$) emitted by an excitation light source. A second value corresponding to the portion of the fluorescent light of an emission wave length ($\lambda_{em}$) emitted by the sample which is incident on the receiving element. The ratio of the second value to the first value is determined. The number of fluorophores in the substance is determined based on the ratio.

18 Claims, 3 Drawing Sheets

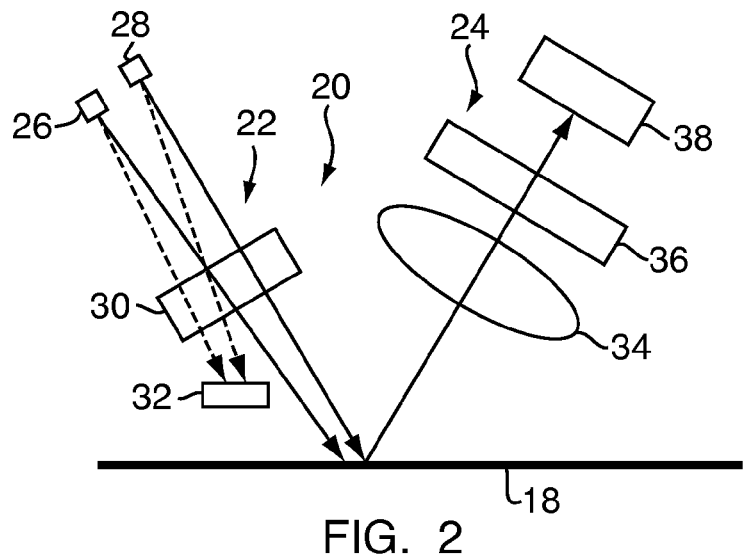
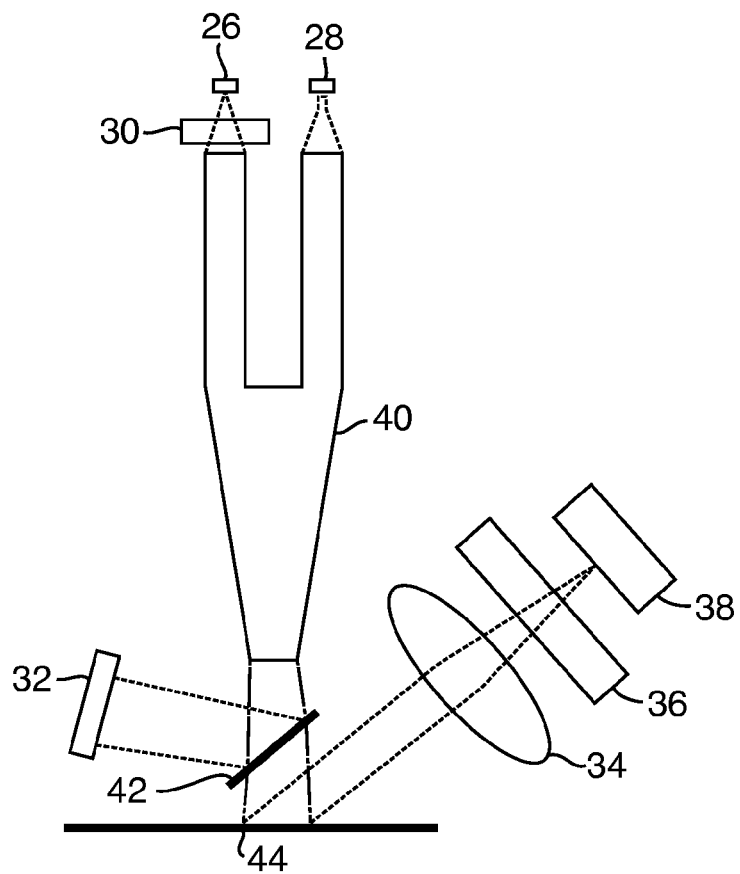
FIG. 2
FIG. 3

METHOD FOR THE QUANTITATIVE DETERMINATION OF THE CONCENTRATION OF FLUOROPHORES OF A SUBSTANCE IN A SAMPLE AND APPARATUS FOR CARRYING OUT THE SAME

CROSS REFERENCE TO RELATED APPLICATION

This application claims the benefit of German Application No. 102008057115.6, filed Nov. 13, 2008, the disclosure of which is herein incorporated by reference in its entirety.

FIELD OF THE INVENTION

The invention concerns a method for the quantitative determination of the concentration of fluorophores of at least one substance in a sample, wherein this substance is irradiated with light of an excitation wave length emitted by an excitation light source and the intensity of the fluorescent light of an emission wave length coming from the sample is measured by means of a receiving element.

BACKGROUND OF THE INVENTION

Normally a so-called fluorescence standard is used for calibrating a measured intensity value of the fluorescent light, which standard emits fluorescent light of a known wave length distribution and intensity when irradiated with excitation light of a preset wave length and intensity. However the long-term stability of this kind of fluorescence standards is usually insufficient. A method and an apparatus for the determination of the fluorescence of a test sample are for instance known from the document EP 0 237 363 A2.

It is therefore the object of the invention to provide a method which guarantees a reliable and repeatable calibration of the measured fluorescent light also over longer periods of time.

SUMMARY OF THE INVENTION

To solve this object it is suggested according to the invention to provide an optical element which couples in a constant portion of a reference light of a reference wave length emitted by a reference light source in the direction of a receiving element. This portion is constant for the optical element also over longer periods of time so that this optical element is suited to constitute a standard of comparison for evaluating a measured value of the detected fluorescent light. A first measured value is detected which corresponds to the portion of the reference light coupled in by the optical element which is incident on the receiving element. Furthermore, the sample is irradiated with excitation light of an excitation wave length emitted by an excitation light source. A second measured value is detected which corresponds to the portion of the fluorescent light of an emission wave length emitted by the sample. Furthermore, the relationship of the second measured value and the first measured value is determined. The number of fluorophores within a detection zone present in the substance of the sample is determined taking this relationship into account.

In the method according to the invention the measured value obtained during the detection of the fluorescent light is thus put into relation to the measured value of the reference light coupled in by the optical element so that the optical element serves as a reference object or reference standard. In order to enable the exact determination of the number of fluorophores of the substance of the sample within a detection zone, a single basic adjustment of the optical element serving as the standard of comparison to a fluorescence standard with a known number of fluorophores within a detection zone can be carried out. In further measurements for the determination of the number of fluorophores within a detection zone a corrected measured value or the number of fluorophores, respectively, can then simply be determined by relating to the optical element.

It is preferable to use a measuring apparatus for determining the number of fluorophores in the substance of a sample within the detection zone. The number of fluorophores in the substance of the sample is determined within the detection zone of the sample with the aid of the detected relationship and with the aid of the relationship of a third measured value and of a fourth measured value detected during a calibration of the measuring apparatus. During the calibration, the constant portion of the reference light emitted by the reference light source is coupled in by the optical element in the direction of the receiving element. At the same time, a third measured value is detected which corresponds to the portion of the light coupled in which is incident on the receiving element. A fluorescence standard is irradiated with the excitation light emitted by the excitation light source. A fourth measured value is detected which corresponds to the portion of the fluorescent light emitted by the fluorescence standard which is incident on the receiving element. In this way, the relationship between the fluorescence standard and the optical element is determined during the calibration process in a simple manner so that the detected measured values of a sample can be related to the optical element. Based on the relationship between the optical element and the fluorescence standard detected during the calibration it is then possible to determine the number of fluorophores of the sample or a corrected measured value which corresponds to the fluorescent light incident on the receiving element.

The optical element is preferably a reflectance standard. Due to its optical properties, such a reflectance standard reflects a constant portion of the incident light at least in one wave length range. Due to this, the reflectance standard can be positioned in lieu of a sample or in lieu of the fluorescence standard and/or besides a sample or besides a fluorescence standard for detecting the measured values.

The number of fluorophores of the sample is preferably determined using the following formula:

$$FD_P = \frac{E_{mes2}}{E_{s2}} \cdot X$$

wherein $FD_P$ denotes the number of fluorophores of the sample within the detection zone;

$E_{mes2}$ denotes a second measured value corresponding to the portion of the fluorescent light of an emission wave length coming from the sample and incident on the receiving element;

$E_{s2}$ denotes a first measured value corresponding to the portion of the light coupled in which is incident on the receiving element; and X denotes a constant scaling factor which represents a relationship between the optical element used and the fluorescence standard and which is determined for the optical element during the calibration of the measuring apparatus.

Also the scaling factor X can be determined using the following equation:

$$X = \frac{E_{s1}}{E_{mes1}} \cdot FD_{FS}$$

wherein $E_{s1}$ denotes a third measured valued corresponding to the constant portion of the reference light emitted by the reference light source and coupled in by the optical element in the direction of the receiving element during the calibration and incident on the receiving element;

$E_{mes1}$ denotes a fourth measured value corresponding to the portion of the fluorescent light emitted by the fluorescence standard which is incident on the receiving element;

$FD_{FS}$ denotes the known number of fluorophores of the fluorescence standard within the detection zone.

It is also advantageous to measure the intensity of the reference light emitted by the reference light source with the help of a further receiving element. Also the intensity of the excitation light emitted by the excitation light source can be measured with the help of this further receiving element. The relationship between the intensity of the excitation light and the intensity of the reference light is then taken into account when determining the number of fluorophores of the sample. Due to this, it is not necessary to use light sources with constant respective light emission, but the light emission of the light sources can vary within a certain range since changes in the light emission are taken into account when evaluating the detected fluorescent light emitted by the sample.

It is also advantageous to use the optical element as a standard of comparison for the calibration of the detected second measured value, whereby in particular contamination, temperature effects and/or deterioration effects of elements of a measuring apparatus for carrying out the method can be compensated with the help of the standard of comparison.

Moreover it is advantageous for the optical path between the reference light source and the optical element used for coupling in the constant portion of the reference light emitted by the reference light source in the direction of the receiving element to pass through the same optical elements as the optical path of the excitation light between the excitation light source and the sample or between the excitation light source and the fluorescence standard, respectively. In this way an arrangement for carrying out the method can have a simple construction. Also, changes in the properties of the optical elements in the optical path affect both the reference light and the excitation light. Alternatively within the optical path of the excitation light an additional filter may be arranged whose transmission range is centered about the excitation wave length. This filter is not positioned within the optical path of the reference light between the reference light source and the optical element.

Moreover it is advantageous to direct the optical paths of the excitation light and of the reference light onto the optical element under different angles. This enables a simple construction of an apparatus for carrying out the method. In particular the space required for arranging the reference light source and the excitation light source is reduced.

Moreover it is advantageous for the optical path between the optical element serving for coupling in the constant portion of the reference light emitted by the reference light source in the direction of the receiving element and the receiving element, to pass through the same optical elements as the optical path of the fluorescent light between the sample and the receiving element or between the fluorescence standard and the receiving element, respectively. Hereby, changes in the optical properties of the optical elements affect the reference light and the fluorescent light in the same way.

Moreover, when calibrating the measuring apparatus for determining the scaling factor it is advantageous to first measure the fluorescence standard with the help of the excitation light using the following equation:

$$E_{mes1} = P_{ex1} \cdot FD_{FS} \cdot K_{ex}$$

wherein $E_{mes1}$ denotes the measured intensity of the fluorescent light emitted by the fluorescence standard;

$P_{ex1}$ denotes the measured intensity of the excitation light;

$FD_{FS}$ denotes the number of the fluorophores of the fluorescence standard within the detection zone; and $K_{ex}$ denotes a proportionality constant;

to subsequently measure the optical element by means of the reference light using the following equation:

$$E_{s1} = P_{em1} \cdot REM \cdot K_{em}$$

wherein $E_{s1}$ denotes the measured intensity of the reference light coupled in by the optical element in the direction of the receiving element;

$P_{em1}$ denotes the measured intensity of the reference light emitted by the reference light source;

REM denotes the constant portion of the reference light coupled in by the optical element in the direction of the receiving element; and $K_{em}$ denotes a proportionality constant;

and to calculate X' from the above using the following equation:

$$X' = \frac{K_{ex}}{K_{em}} = \frac{E_{mes1}}{E_{s1}} \cdot \frac{P_{em1}}{P_{ex1}} \cdot \frac{REM}{FD_{FS}}$$

X' differs from X in that the measured light intensities of the excitation light and of the reference light are taken into account as well. Thus the factor X can be used preferably in measuring arrangements comprising a stabilized reference light source and a stabilized excitation light source which each emit reference light or excitation light, respectively, with a constant intensity.

The sample and the optical element can be preferably measured by means of a scanning method. Alternately also a non-scanning measuring of the sample and the optical element is possible.

An apparatus for carrying out the method preferably includes a carrier for a sample to be measured, an emission branch comprising an excitation light source for emitting excitation light of an excitation wave length, a first receiving element for measuring the intensity of the excitation light and a first filter arranged within the path of the excitation light, the transmission range of which filter is centered about the excitation wave length, as well as a receiving branch comprising a second receiving element for measuring the intensity of the fluorescent light of an emission wave length coming from the sample, and a second filter whose transmission range is centered about the emission wave length. In this arrangement, a reference light source for emitting at least one reference beam of the emission wave length is arranged within the emission branch. The first receiving element serves to measure the intensity of the light of both light sources of the emission branch. In the apparatus an optical element is arranged so that it receives the light of the reference light source of the emission branch. With such a relatively simple configuration of the apparatus the number of fluorophores of a sample can be detected within a detection zone in a simple manner while changes in the properties of the apparatus can be compensated based on the reference measuring with the help of the optical element. The emission branch and the receiving branch are preferably combined to form an optical module which can be adjusted relative to the optical element and to the sample carrier. Moreover it is advantageous to arrange the first receiving element between the first filter and the sample carrier or between the first filter and the optical element, respectively.

Since the intensity of the fluorescent light can be smaller by several orders of magnitude when compared to the excitation light, scattered excitation light or other extraneous light must be prevented from reaching the receiving element. In general, filters are used for this purpose, which are chosen such that a filter arranged within the excitation light beam generally only transmits the wave length of the excitation light while a filter arranged in the measuring branch generally only transmits the wave length of the fluorescent light. For this reason in an advantageous embodiment of the solution according to the invention reference light of the emission wave length, i.e. the wave length of the fluorescent light, is used for measuring the optical element.

The two light sources of the emission branch can be arranged so that the optical paths of the light beams of the two light sources of the emission branch are at least approximately identical. However, they may instead be arranged in such a way that the optical paths of the excitation light and of the reference light are directed onto the reflectance standard under different angles. In the first case, the reference light source has to have a higher intensity, since the reference light also passes through the filter arranged within the excitation light beam whose transmission range corresponds in general to the excitation wave length and thus considerably attenuates the intensity of the reference light of the emission wave length. This is avoided in the second case.

In the method according to the invention thus a calibration can be carried out with the help of an optical element or of a reflectance standard which can be produced with the desired long-term stability. It is sufficient to carry out a single adjustment of this optical element with the help of an adjusted fluorescence standard during a starting-up calibration of a measuring apparatus for carrying out the method. Subsequently the fluorescence density of a sample can always be determined with reference to a deposited internal optical element or reflectance standard. The starting-up calibration is for example carried out at the place of manufacture of the measuring apparatus before delivering the measuring apparatus to the customer or alternately during a start-up or reconnection of the measuring apparatus at the location of the customer or user. The aim of such a starting-up calibration is in particular to minimize a variation of the measuring results between several produced measuring apparatus and/or to enable traceability of the measuring results of a measuring apparatus to an authoritative standard with long-term stability or to a collective of several measuring apparatus. When tracing the measuring results of a measuring apparatus back to a collective of several measuring apparatus, the measuring results of all measuring apparatus of the collective can be compared to each other in a simple manner.

For implementing a measuring apparatus, two alternative approaches are possible:

1. The fluorescence standard $FD_{FS}$ is used as a comparison standard for the starting-up calibration during the start-up of each single measuring apparatus. This requires that this fluorescence standard is highly stable or that it can be verified with the help of a reference device and that the changes in the properties of the fluorescence standard detected during verification are being taken into account during the starting-up calibration.

2. The fluorescence standard $FD_{FS}$ is used when starting up a reference measuring apparatus. Then an optical element, in particular a reflectance standard, is measured with the help of the reference measuring apparatus and a relationship between the fluorescence standard and the optical properties of the optical element, in particular the reflectance properties of the reflectance standard, is determined. In this way, a definite correlation between the reflectance values of the optical element and the fluorescence properties of the fluorescence standard $FD_{FS}$ is determined which is then preset in further measuring apparatus as the correlation between the reflectance values of optical elements provided in these further measuring apparatus. The optical elements of the further measuring apparatus have the same optical reflectance properties as the optical element of the reference measuring apparatus. For determining the fluorescence properties of a sample to be examined, the scaling factor X or X' is then used as has been explained in detail above. The fluorescence standard $FD_{FS}$ is not necessarily an indicator of the number of fluorophores per surface area or the fluorophore density. Instead, $FD_P$ can be a general measure of the concentration of a substance within a sample.

The apparatus can be modified to include further features which are indicated in particular with respect to the method according to the invention. In particular the apparatus can be modified to include the features of the dependent method claims or corresponding apparatus features.

BRIEF DESCRIPTION OF THE DRAWINGS

Further features and advantages of the invention become clear from the following description of embodiments in connection with the enclosed drawing figures. In the drawings:

FIGS. 2 and 3 show schematic depictions of two embodiments of measuring arrangements for carrying out the method according to the invention.

DESCRIPTION OF THE PREFERRED EMBODIMENTS

Figure 1:
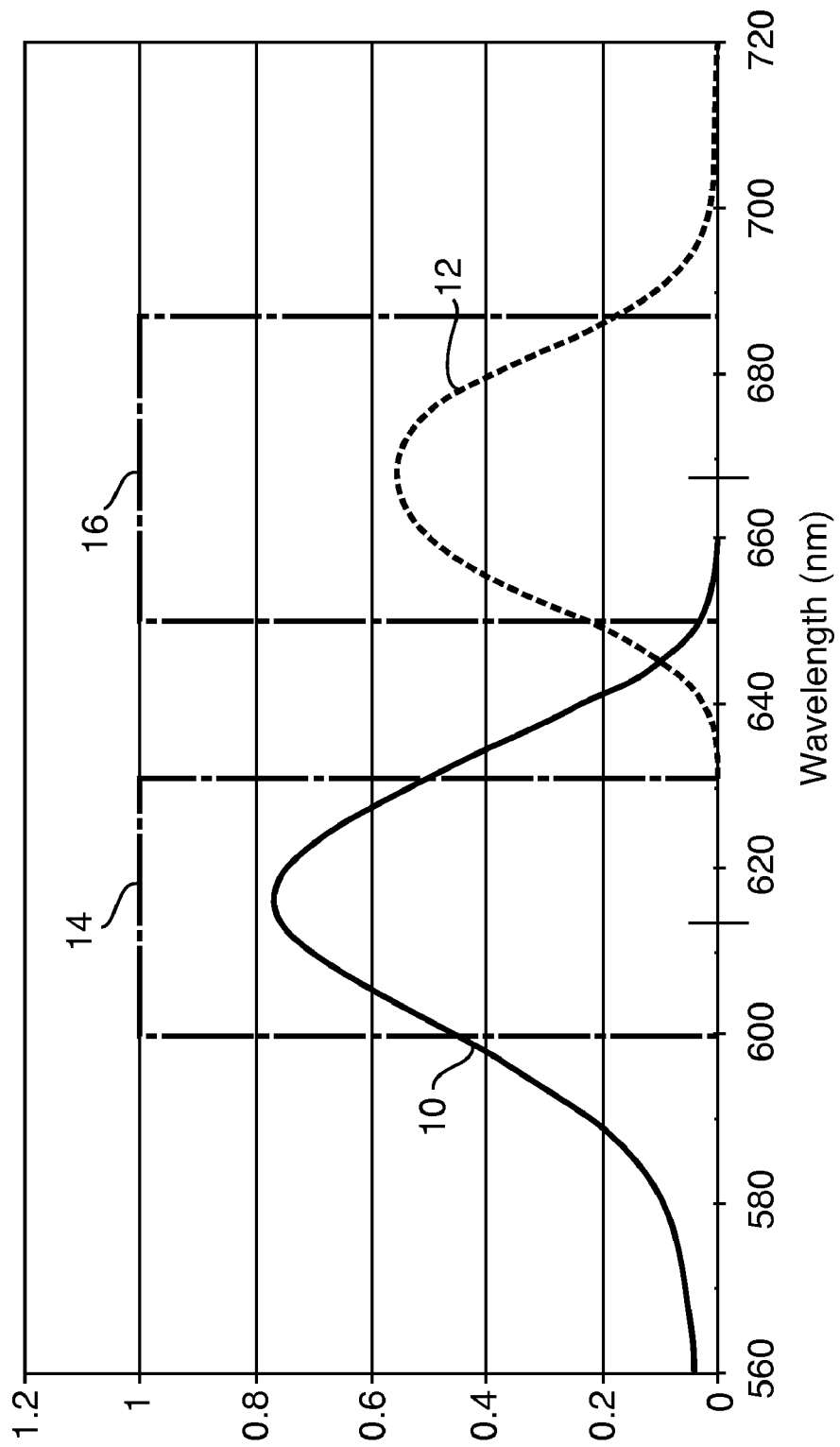
FIG. 1 shows the wave length distribution of the excitation light and of the fluorescent light as well as the filter characteristics of the respective interference filters for the excitation light and the fluorescent light.

FIG. 1 shows the gradient of efficiency of the excitation light with reference to the wave length by means of a graph 10, as well as the emission characteristic of the corresponding fluorescent light by means of a graph 12. Moreover, a rectangle 14 represents the filter characteristic of the excitation branch or emission branch, while the rectangle 16 represents the filter characteristic of a receiving or measuring branch. When the Stokes shift is small, as shown in FIG. 1, interference filter with very steep edges are preferably used as filters 14 and 16. The interference filters for the excitation branch are preferably dimensioned such that maximum excitation efficiency is reached and the wave length of the excitation light source is within the transmission range of the filter.

In the embodiment of FIG. 2, reference number 18 denotes schematically a carrier for a sample to be measured or a reflectance standard, respectively. Above this plane 18 an optical module, generally indicated at 20, is arranged which comprises an emission branch 22 and a receiving or measuring branch 24.

The emission branch 22 comprises a first light source or excitation light source 26, which emits light of the excitation wave length $\lambda_{ex}$. Next to it there is a second light source or reference light source 28, which emits light of the reference wave length $\lambda_{em}$. This wave length generally corresponds to the wave length of the fluorescent light emitted by the excited sample and thus lies within the filter characteristic 16. The two light sources can be LEDs. The beams of both light sources 26 and 28 pass through a filter 30 which has the filter characteristic 14 of FIG. 1. Since the reference wave length $\lambda_{em}$ lies outside the filter characteristic 14, the reference light is attenuated by a factor of 100 to 1,000,000. For this reason, the output power of the reference light source is preferably considerably higher than that of the excitation light source 26. The intensities of both light sources 26 and 28 are read by a monitor diode presenting a first receiving element 32. The receiving branch 24 has an optics 34, a filter 36 with the filter characteristic 16, as well as a photo diode 38 serving as a second receiving element.

Before the actual measuring of a sample takes place, a reflectance standard is measured. The reference beam emitted by the reference light source 28 is used for this purpose. Although the wave length $\lambda_{em}$ of the reference light is attenuated by the filter 30, the reflectance of the reflectance standard reaches the photo diode 38 without obstructions. Since the reflectance is higher by several orders of magnitude than the fluorescence, a major part of the attenuation of the reference light by the filter 30 is compensated for. The performance at the photo diode 38 can therefore be compared to the performance of the fluorescence emission of the sample. The monitor diode 32 however is activated considerably less by the reference light source 28 than by the excitation light source 26. In an integrated measuring method this can be partially compensated for by means of different lengths of integration times. Also measuring methods exist which provide a measuring range of about 200 even with constant integration times at a signal-to-noise ratio of 100. A combination of different integration times and measuring ranges should make it possible to reach an intensity difference of the two light sources at the monitor diode 32 of about 50,000 with a signal-to-noise ratio of 100.

While measuring of the reflectance standard, i.e. the internal standard, is carried out using light of the wave length $\lambda_{em}$, the actual fluorescence measurement is performed with light of the wave length $\lambda_{ex}$. The calibration of the measuring results is carried out by referencing them to the measuring of the internal standard. To make this approach valid, the beam paths of the reference light and of the excitation light should be nearly identical as is the case in the embodiment of FIG. 1. For this purpose it is practical to use very small light sources such as SMD-LEDs. The light paths within the receiving branch are nearly identical since during the excitation of the fluorescence the emitted wave length corresponds to the reference wave length. The respective projection is identical. The transmission by the filter 36 can vary slightly, since the spectrum of the emission is broader than the spectrum of the reference light source. However, this is a constant which does not change with time. Also the temperature gradation is insignificantly small.

In the embodiment shown in FIG. 3 the light of the reference light source 28 is fed into a light conductor 40 separately from the excitation light source 26. The light conductor 40 homogenizes the light so that the respective intensity distributions of the two light sources are almost identical at the outlet. A portion of the light is coupled out by means of a beam splitter 42 and directed to the monitor diode 32. The beam splitter 42 can also be omitted and the light can be coupled out separately from the light conductor 40 and directed to the monitor diode 32. The light distribution is nearly identical for the two wave lengths $\lambda_{ex}$ and $\lambda_{em}$ at the point 44 on the sample or on the reflectance standard, respectively.

The advantage of the embodiment according to FIG. 3 as compared to the embodiment according to FIG. 2 lies in the fact that the reference light does not pass through the filter 30 and is consequently not attenuated. Therefore a weaker reference light source may be used. The relationship of the light intensities at the monitor diode 32 and at the photo diode 38 can be controlled via the output power of the reference light source.

Figure 4:
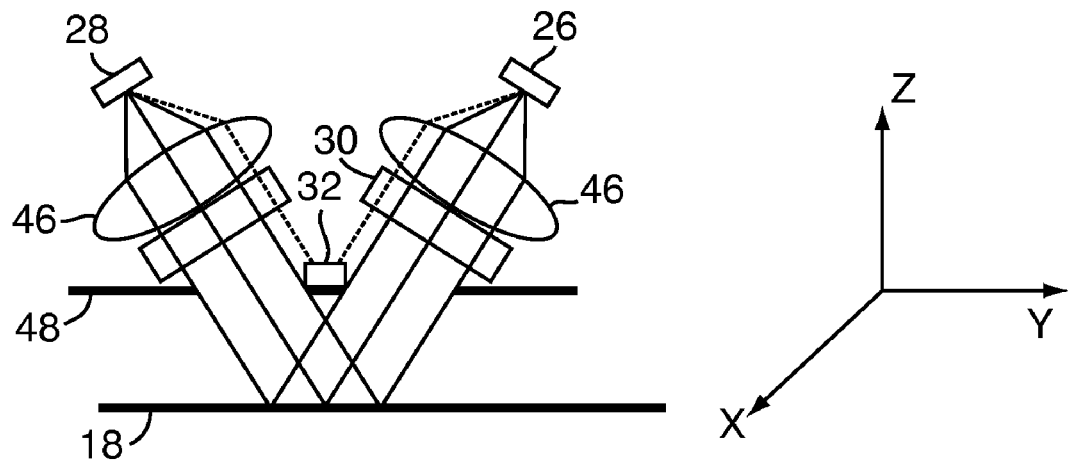
FIGS. 4 and 5 show depictions of two further embodiments of the emission branch of an apparatus for carrying out the method according to the invention.

FIG. 4 shows only the emission branch 22 of the measuring arrangement. In this branch the light beams of both light sources 26 and 28 are being collimated by respective lenses 46. The light beams are only combined with each other upon reaching the measuring plane 18. The filter 30 is only arranged in the excitation light beam. The reference light reaches the measuring plane 18 without being attenuated by a filter. The performance of both light sources is again measured by means of a monitor diode 32 which is arranged directly in the illumination beam path. However, this does not impede the illumination of the measuring field whose size is determined via an aperture 48. The projection optics, i.e. the receiving branch 24, is not shown in this case. The optical axis of the receiving branch is tilted in the x-z-plane, while the optical axis of illumination is tilted in the z-y-plane as shown in FIG. 4.

Figure 5:
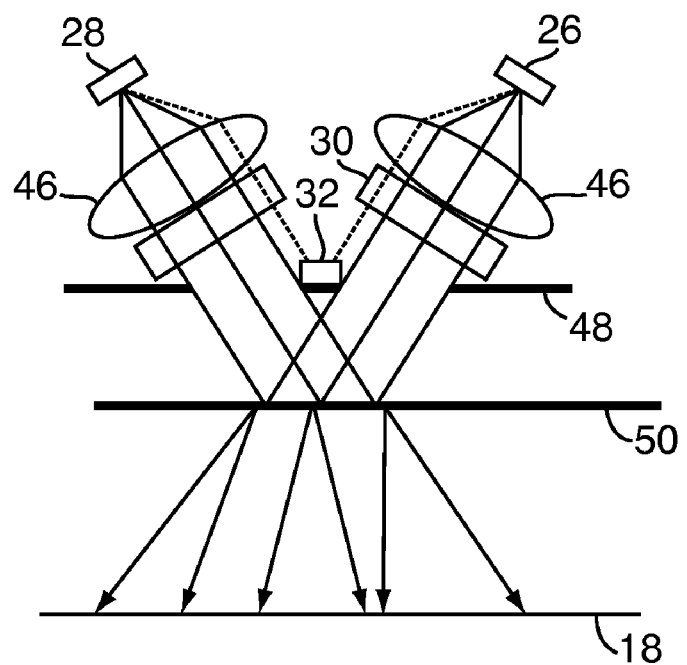

FIG. 5 shows an embodiment which is preferably used in non-scanning systems. In this embodiment, the measuring field is completely illuminated and the fluorescent light is imaged onto a two-dimensional sensor. As in the depiction of FIG. 4, the receiving branch is not shown. In order to achieve uniform illumination, preferably a diffusion disk 50 is used. Otherwise the construction of this embodiment is similar to the embodiment according to FIG. 4. However, here the diffusion disk 50 and not the measuring field is illuminated directly. Due to this construction, the illumination distribution in the measuring plane 18 should be almost identical for both wave lengths $\lambda_{ex}$ and $\lambda_{em}$.

As described above, in a scanning system the internal standard is measured with the help of the reference light source before the actual measurement takes place. In a non-scanning system which e.g. includes flat area illumination and a 2-D-sensor for the receiving branch, the remission measurement can be carried out with a QC-element (quality cartridge) which instead of the fluorescence measuring field has a defined remission. Although the QC-measurement is then not carried out before each measurement, with this measure deterioration effects of the light source or contamination of the optics can be identified early on.

In order to be able to carry out fluorescence measurements related to reflectance values with the apparatus according to FIGS. 2 to 5, when starting up the apparatus a calibration has to be carried out. In the following, this calibration is explained with reference to a scanning system comprising an integrated internal reflectance standard. This description may however also be applied to a non-scanning system without alterations.

Instead of the internal reflectance standard, preferably a QC-element based on reflectance is used there.

Normally, the calibration measurement is only needed to be carried out once. A device in a laboratory or in the field then always relates to the internal remission standard. Before starting up a device the following steps are carried out:

First an external fluorescence standard is measured using the excitation light source 26:

$$E_{mes1} = P_{ex1} \cdot FD_{FS} \cdot K_{ex}$$

wherein $P_{ex1}$ = the intensity of the excitation light measured with the help of the monitor diode 32;

$FD_{FS}$ = the number of fluorophores of the fluorescence standard within the detection zone;

$E_{mes1}$ = the intensity of the fluorescent light emitted by the fluorescence standard and measured with the help of the photo diode 38; and $K_{ex}$ = a proportionality constant to be determined using the above equation.

The factor $K_{ex}$ indicates how efficiently the performance of the excitation wave length $\lambda_{ex}$ is transformed into fluorescence. Since normally not the entire performance of the illumination in the measuring field plane is measured by the monitor diode 32, also the ratio of measured performance to total performance is included in this factor.

Moreover the internal reflectance standard of the apparatus is measured using the reference light source 28:

$$E_{s1} = P_{em1} \cdot REM \cdot K_{em}$$

wherein $P_{em1}$ = the intensity of the reference light measured with the help of the monitor diode 32;

REM = the constant portion of the reference light coupled in by the optical element in the direction of the receiving element 38;

$E_{s1}$ = the measured intensity of the reference light coupled in by the optical element in the direction of the receiving element 38;

$K_{em}$ = a proportionality constant to be determined using the above equation.

The two proportionality factors $K_{ex}$ and $K_{em}$ are related to each other via the constant X which is to be determined in the following:

$$K_{ex} = X \cdot K_{em}$$

A condition for further calculation is that the relationship between $K_{em}$ and $K_{ex}$ remains constant. Since only the relationship between $P_{ex}$ and $P_{em}$ is relevant for the following constant X and not their absolute values, this assumption should be correct. Contamination of the optics e.g. affects $K_{ex}$ and $K_{em}$ in the same way so that the constant X is not influenced by it.

The constant X is determined directly after the calibration:

$$X' = \frac{K_{ex}}{K_{em}} = \frac{E_{mes1}}{E_{s1}} \cdot \frac{P_{em1}}{P_{ex1}} \cdot \frac{REM}{FD_{FS}}$$

With the determination of the constant X' all fluorescence measurements can now be related to an internal reflectance standard, which, as opposed to an internal fluorescence standard, provides long-term stability. Thus the following equation for the number of fluorophores in at least one substance of the sample within a detection zone is obtained, which number is a measure $FD_P$ for the concentration of a substance in a measured sample within the detection zone:

$$FD_P = \frac{1}{X'} \cdot \frac{E_{mes2}}{E_{s2}} \cdot \frac{P_{em2}}{P_{ex2}} \cdot REM$$

For this equation during the measuring of the reflectance standard the measurements $P_{em2}$ and $E_{s2}$ are determined. During the measuring of the sample, the values $E_{mes2}$ and $P_{ex2}$ are measured. Thus only the measured signal strengths $E_{s2}$, $E_{mes2}$ and the relationship measurements of the intensity measurements $P_{em2}$ and $P_{ex2}$ are included in the calculation. The constant X' and the value REM of the reflectance standard are known.

The receiving elements mentioned above may be photo diodes, line sensors, area sensors or also photo-multipliers. In scanning systems preferably photodiodes and line sensors are used.

The photodiode 32 can also be used for stabilizing the performance of the light sources. In light emitting diodes the optical output performance normally is reduced due to heating processes during operation. These effects can be reduced by performing a corresponding loop control. Also deterioration processes of the LEDs can be compensated for in this manner. The test strips or sample carriers are thus always irradiated with the same power and possible bleaching always occurs under the same conditions.

Although laser diodes as a rule comprise an internal monitor diode, which can be used for performance control, the stability which can be reached in this manner is often not sufficient.

The invention claimed is:

1. A method for the quantitative determination of a concentration of fluorophores of at least one substance in a sample, comprising:
   coupling in a constant portion of a reference light of a reference light wave length ($\lambda_r$) emitted by a reference light source by an optical element in a direction of a first receiving element,
   detecting a first measured value ($E_{s2}$) corresponding to the portion of the reference light coupled in and incident on the first receiving element,
   irradiating the sample with the excitation light of an excitation wave length ($\lambda_{ex}$) emitted by an excitation light source,
   detecting a second measured value ($E_{mes2}$) corresponding to a portion of a fluorescent light of an emission wave length ($\lambda_{em}$) emitted by the sample and incident on the first receiving element,
   determining a ratio ($E_{mes2}/E_{s2}$) of the second measured value ($E_{mes2}$) to the first measured value ($E_{s2}$), and
   determining a number of the fluorophores in the substance of the sample within a detection zone taking the ratio ($E_{mes2}/E_{s2}$) into account,
   wherein an optical path of the constant portion of the reference light between the optical element and the first receiving element is the same as an optical path of the fluorescent light between the sample and the first receiving element.

2. The method according to claim 1, wherein a measuring apparatus is used for the determination of the number of fluorophores in the substance of the sample within the detection zone,
   wherein the number of fluorophores in the substance of the sample within a detection zone is determined with the help of the detected ratio ($E_{mes2}/E_{s2}$) and of the ratio ($E_{s1}/E_{mes1}$) of a third measured value ($E_{s1}$) to a fourth measured value ($E_{mes1}$) detected during a calibration of the measuring apparatus, wherein during the calibration the constant portion of the reference light emitted by the reference light source is coupled in by the optical element in the direction of the first receiving element and a third measured value ($E_{s1}$) is detected which corresponds to the portion of the light coupled in which is incident on the first receiving element, wherein a fluorescence standard is irradiated with the excitation light emitted by the excitation light source and a fourth measured value ($E_{mes1}$) is detected which corresponds to the portion of the fluorescent light emitted by the fluorescence standard which is incident on the first receiving element.

3. The method according to claim 1, wherein a reflectance standard is used as the optical element.

4. The method according to claim 1, wherein the optical element is used as a standard of comparison for calibrating the detected second measured value ($E_{mes2}$), the standard of comparison being used to compensate for at least one of contamination, temperature effects and deterioration effects of elements of a measuring apparatus for carrying out the method.

5. The method according to claim 1, wherein the number of fluorophores of the sample is determined using the following formula:

$$FD_P = \frac{E_{mes2}}{E_{s2}} \cdot X$$

wherein $FD_P$ denotes the number of fluorophores of the sample;

$E_{mes2}$ denotes a second measured value corresponding to the portion of the fluorescent light of an emission wave length coming from the sample and incident on the first receiving element;

$E_{s2}$ denotes a first measured value corresponding to the portion of the light coupled in which is incident on the first receiving element; and X denotes a constant scaling factor which represents a relationship between the optical element used and a fluorescence standard and which is determined for the optical element during the calibration of the measuring apparatus.

6. The method according to claim 5, wherein the scaling factor X is determined using the following equation:

$$X = \frac{E_{s1}}{E_{mes1}} \cdot FD_{FS}$$

wherein $E_{s1}$ denotes a third measured value corresponding to the constant portion of the reference light emitted by the reference light source and coupled in by the optical element in the direction of the first receiving element during calibration which is incident on the first receiving element;

$E_{mes1}$ denotes a fourth measured value corresponding to the portion of the fluorescent light emitted by the fluorescence standard and incident on the first receiving element; and $FD_{FS}$ denotes the known number of fluorophores of the fluorescence standard within the detection zone.

7. The method according to claim 1, wherein the optical path between the reference light source and the optical element is the same as the optical path of the excitation light between the excitation light source and the sample.

8. The method according to claim 1, wherein a filter is arranged in the optical path of the excitation light between the excitation light source and the sample, wherein a transmission range of the filter is centered about the excitation wave length ($\lambda_{ex}$), and wherein the filter is not arranged in the optical path of the reference light between the reference light source and the optical element.

9. The method according to claim 1, wherein the optical paths of the excitation light and of the reference light are directed towards the optical element under different angles.

10. The method according to claim 1, wherein an intensity of the reference light source and an intensity of the excitation light source are measured with the help of a second receiving element and are used for the performance control of the two light sources.

11. The method according to claim 1, wherein the intensity ($P_{em}$) of the reference light emitted by the reference light source (28) is measured with the help of a second receiving element, wherein the intensity ($P_{ex}$) of the excitation light emitted by the excitation light source is measured with the help of the second receiving element, and wherein a ratio of the intensity of the excitation light to the intensity of the reference light is taken into account when determining the number of fluorophores of the sample.

12. The method according to claim 2, wherein in the calibration of the measuring apparatus, for determining the scaling factor X' first the fluorescence standard is measured with the help of the excitation light according to the following equation:

$$E_{mes1} = P_{ex1} \cdot FD_{FS} \cdot K_{ex}$$

wherein $E_{mes1}$ denotes the measured intensity of the fluorescent light emitted by the fluorescence standard;

$P_{ex1}$ denotes the measured intensity of the excitation light;

$FD_{FS}$ denotes the number of the fluorophores of the fluorescence standard within the detection zone; and $K_{ex}$ denotes a proportionality constant;

wherein subsequently the constant portion of the reference light coupled in by the optical element is measured according to the following equation:

$$E_{s1} = P_{em1} \cdot REM \cdot K_{em}$$

wherein $E_{s1}$ denotes the measured intensity of the reference light coupled in by the optical element in the direction of the first receiving element;

$P_{em1}$ denotes the measured intensity of the reference light emitted by the reference light source;

REM denotes the constant portion of the reference light coupled in by the optical element in the direction of the first receiving element; and $K_{em}$ denotes a proportionality constant;
and wherein X' is calculated from this using the following equation:

$$X' = \frac{K_{ex}}{K_{em}} = \frac{E_{mes1}}{E_{s1}} \cdot \frac{P_{em1}}{P_{ex1}} \cdot \frac{REM}{FD_{FS}}.$$

13. The method according to claim 12, wherein the number of fluorophores in the at least one substance of the sample is detected within the detection zone using the following equation:

$$FD_P = \frac{1}{X'} \cdot \frac{E_{mes2}}{E_{s2}} \cdot \frac{P_{em2}}{P_{ex2}} \cdot REM$$

wherein $FD_P$ is a measure of the number of fluorophores within the detection zone.

14. The method according to claim 1, wherein at least one of the sample and the optical element are measured using a scanning method.

15. The method according to claim 1, wherein at least one of the sample and the optical element are measured using a non-scanning method.

16. An apparatus for carrying out a quantitative determination of a concentration of fluorophores of at least one substance in a sample, comprising:
a carrier for a sample to be measured,
an emission branch including an excitation light source for emitting excitation light of an excitation wave length ($\lambda_{ex}$), a first receiving element for measuring an intensity ($P_{ex}$) of the excitation light, and a first filter arranged in a path of the excitation light, wherein a transmission range of the first filter is centered about the excitation wave length ($\lambda_{ex}$), and
a receiving branch comprising a second receiving element for measuring an intensity ($E_{mes2}$) of the fluorescent light of an emission wave length ($\lambda_{em}$) coming from the sample, and a second filter having a transmission range centered about the emission wave length ($\lambda_{em}$),
wherein the emission branch comprises a reference light source for emitting a reference light of the emission wave length ($\lambda_{em}$),
wherein the first receiving element is arranged in the emission branch for measurement of the intensities of the light of both light sources, and
wherein an optical element is arranged in the apparatus such that the optical element receives the reference light of the reference light source of the emission branch, and
wherein an optical path of the reference light between the optical element and the second receiving element is the same as an optical path of the fluorescent light between the sample and the second receiving element.

17. The apparatus according to claim 16, wherein the emission branch and the receiving branch are combined to form an optical module which can be adjusted relative to the optical element and to the carrier for the sample.

18. The apparatus according to claim 16, wherein the first receiving element is arranged between the first filter and at least one of the carrier for the sample and the optical element.

* * * * *